US006770799B2

(12) United States Patent
Mor et al.

(10) Patent No.: US 6,770,799 B2
(45) Date of Patent: Aug. 3, 2004

(54) EXPRESSION OF RECOMBINANT HUMAN ACETYLCHOLINESTERASE IN TRANSGENIC PLANTS

(76) Inventors: Tsafrir S. Mor, Department of Plant Biology, Room 637, Arizona State University, P.O. Box 871601, Tempe, AZ (US) 85287-1601; Hermona Soreq, Department of Biological Chemistry, The Hebrew University of Jerusalem, Jerusalem (IL), 91904; Charles J. Arntzen, Department of Plant Biology, Room 637, Arizona State University, P.O. Box 871601, Tempe, AZ (US) 85287-1601; Hugh S. Mason, 1311 Hanshaw Rd., Ithaca, NY (US) 14850

( * ) Notice: Subject to any disclaimer, the term of this patent is extended or adjusted under 35 U.S.C. 154(b) by 116 days.

(21) Appl. No.: 09/810,861

(22) Filed: Mar. 16, 2001

(65) Prior Publication Data

US 2002/0162140 A1 Oct. 31, 2002

Related U.S. Application Data

(60) Provisional application No. 60/190,440, filed on Mar. 17, 2000.

(51) Int. Cl.[7] ............................ A01H 1/00; A01H 5/00; C07H 21/02; C07H 21/04; C12N 5/00

(52) U.S. Cl. .................... 800/288; 800/317.4; 435/423; 536/23.1

(58) Field of Search .............................. 800/288, 317.4, 800/295; 435/423, 419; 536/23.1

(56) References Cited

U.S. PATENT DOCUMENTS 4,956,282 A * 9/1990 Goodman et al.
5,595,903 A * 1/1997 Seroq et al.
5,891,725 A * 4/1999 Seroq et al.

OTHER PUBLICATIONS

Meisssner, R. et al, 1997, "A new model system for tomato genetics", the Plant Journal, 12(6), 1465–1472.
Haq, T. et al, 1995, "Oral Immunization with a Recombinant Bacterial Antigen Produced in Transgenic Plants", Science, vol. 268, pp 714–716.
Aziz–Aloya, R. et al, 1993, "Expression of a human acetylcholinesterase promoter–reporter construct in developing neuromuscular junctions of Xenopus embryos", Proc. Natl. Acad. Sci., vol. 90, pp 2471–2475.
Sroeq, H. et al, 1990, "Molecular cloning and construction of the coding region for human acetylcholinesterase reveals a G+C–rich attenuating structure", Proc. Natl. Acad. Sci., vol. 87, pp. 9688–9692.

* cited by examiner

*Primary Examiner*—Elizabeth F. McElwain
*Assistant Examiner*—Georgia L Helmer
(74) *Attorney, Agent, or Firm*—Brown & Michaels, PC

(57) ABSTRACT

Briefly stated, the invention includes a method of making a transgenic plant that is capable of expressing a physiologically active human acetylcholinesterase, comprising the steps of introducing into at least one plant cell a polynucleotide that encodes a human acetylcholinesterase, and regenerating from the plant cell a transgenic plant that is capable of expressing a physiologically active human acetylcholinesterase in at least one tissue type of the transgenic plant. Another embodiment of the invention includes a method of making a physiologically active human acetylcholinesterase, comprising the steps of introducing into at least one plant cell a polynucleotide that encodes a human acetylcholinesterase, regenerating from the plant cell a transgenic plant that is capable of expressing a physiologically active human acetylcholinesterase in at least one tissue type of the transgenic plant, and isolating or purifying from the transgenic plant or a part thereof a physiologically active human acetylcholinesterase.

11 Claims, 5 Drawing Sheets

SEQUENCE LISTING

<160> NUMBER OF SEQ ID NOS: 5

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: primer pAChE-Nco, derived from human AChE gene and modified to introduce an Nco I restriction site.

<400> SEQUENCE: 1
gatatctgca gccatggcta ggccccccgc 29

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: primer pAChE-Kpn, derived from human AChE gene and modified to introduce a Kpn I restriction site.

<400> SEQUENCE: 2
cggtacctat caggtagcgc tgagcaattt g 31

<210> SEQ ID NO 3
<211> LENGTH: 5767
<212> TYPE: DNA
<213> ORGANISM: Artificial Sequence
<220> FEATURE:
<223> OTHER INFORMATION: Description of Artificial Sequence: plasmid vector pTM034.

<400> SEQUENCE: 3
agcttgcatg cctgcaggtc aacatggtgg agcacgacac tctcgtctac tccaagaata 60
tcaaagatac agtctcagaa gaccagaggg ctattgagac ttttcaacaa agggtaatat 120
cgggaaacct cctcggattc cattgcccag ctatctgtca cttcatcgaa aggacagtag 180
aaaaggaaga tggcttctac aaatgccatc attgcgataa aggaaaggct atcgttcaag 240
aatgcctcta ccgacagtgg tcccaaagat ggacccccac ccacgaggaa catcgtggaa 300
aaagaagacg ttccaaccac gtcttcaaag caagtggatt gatgtgataa cttttcaaca 360
aagggtaata tcgggaaacc tcctcggatt ccattgccca gctatctgtc acttcatcga 420
aaggacagta gaaaaggaag atggcttcta caaatgccat cattgcgata aaggaaaggc 480
tatcgttcaa gaatgcctct accgacagtg gtcccaaaga tggaccccca cccacgagga 540
acatcgtgga aaaagaagac gttccaacca cgtcttcaaa gcaagtggat tgatgtgata 600
tctccactga cgtaagggat gacgcacaat cccactatcc ttcgcaagac ccttcctcta 660
tataaggaag ttcatttcat ttggagagga cctcgagaat taattctcaa cacaacatat 720
acaaaacaaa cgaatctcaa gcaatcaagc attctacttc tattgcagca atttaaatca 780
tttcttttaa agcaaaagca attttctgaa aattttcacc atttacgaac gatagccatg 840
gctcccccgc agtgtctgct gcacacgcct tccctggctt ccccactcct tctcctcctc 900
ctctggctcc tgggtggagg agtgggggct gagggccggg aggatgcaga gctgctggtg 960
acggtgcgtg gggccggct gcggggcatt cgcctgaaga cccccggggg ccctgtctct 1020
gctttcctgg gcatcccctt tgcggagcca cccatgggac cccgtcgctt tctgccaccg 1080

-continued gagcccaagc agccttggtc aggggtggta gacgctacaa ccttccagag tgtctgctac 1140
caatatgtgg acaccctata cccaggtttt gagggcaccg agatgtggaa ccccaaccgt 1200
gagctgagcg aggactgcct gtacctcaac gtgtggacac catacccccg gcctacatcc 1260
cccacccctg tcctcgtctg gatctatggg ggtggcttct acagtggggc ctcctccttg 1320
gacgtgtacg atggccgctt cttggtacag gccgagagga ctgtgctggt gtccatgaac 1380
taccgggtgg gagcctttgg cttcctggcc ctgccgggga gccgagaggc cccgggcaat 1440
gtgggtctcc tggatcagag gctggccctg cagtgggtgc aggagaacgt ggcagccttc 1500
gggggtgacc cgacatcagt gacgctgttt ggggagagcg cgggagccgc ctcggtgggc 1560
atgcacctgc tgtccccgcc cagccggggc ctgttccaca gggccgtgct gcagagcggt 1620
gcccccaatg gaccctgggc cacggtgggc atgggagagg cccgtcgcag ggccacgcag 1680
ctggcccacc ttgtgggctg tcctccaggc ggcactggtg ggaatgacac agagctggta 1740
gcctgccttc ggacacgacc agcgcaggtc ctggtgaacc acgaatggca cgtgctgcct 1800
caagaaagcg tcttccggtt ctccttcgtg cctgtggtag atggagactt cctcagtgac 1860
accccagagg ccctcatcaa cgcgggagac ttccacggcc tgcaggtgct ggtgggtgtg 1920
gtgaaggatg agggctcgta ttttctggtt tacggggccc caggcttcag caaagacaac 1980
gagtctctca tcagccgggc cgagttcctg gccggggtgc gggtcggggt tccccaggta 2040
agtgacctgg cagccgaggc tgtggtcctg cattacacag actggctgca tcccgaggac 2100
ccggcacgcc tgagggaggc cctgagcgat gtggtgggcg accacaatgt cgtgtgcccc 2160
gtggcccagc tggctgggcg actggctgcc cagggtgccc gggtctacgc ctacgtcttt 2220
gaacaccgtg cttccacgct ctcctggccc ctgtggatgg gggtgcccca cggctacgag 2280
atcgagttca tctttgggat ccccctggac cccctctcga actacacggc agaggagaaa 2340
atcttcgccc agcgactgat gcgatactgg gccaactttg cccgcacagg ggatcccaat 2400
gagccccgag accccaaggc cccacaatgg cccccgtaca cggcgggggc tcagcagtac 2460
gttagtctgg acctgcggcc gctggaggtg cggcgggggc tgcgcgccca ggcctgcgcc 2520
ttctggaacc gcttcctccc caaattgctc agcgctacct gataggtacc gagctctctc 2580
aacaatctag ctagagtttg ctcctatcta tatgtaataa ggtatgctga tatgcactat 2640
tcaaatagga gcattagcta tgtttgttaa tgtcacttta tgttatgtgg gtaagtcacc 2700
taagacactc cacgtaccta cgttgttgtc tcttaccggc tttaataaat cttctgccct 2760
tgttccatat ttactaatta tccctttctt cactaaaaga aaattgttat cattaagtat 2820
tagtctttag aacatatgag gtctttaatt gggtaggttt tacaaattaa ctaatataaa 2880
atgtcataaa atccacgtgg ttaaacaaat gcagaaaatc gacgtcgtct attggaccga 2940
cagttgctat taatataatg ggccaccata gtagactgac aaataaatta cctgacaaca 3000
tcgtttcact aaataacaaa cacaaaaagg gagtgcattt tccagggcat ttttgtaata 3060
aaaaacagtt aaaagggagt gcaatagaaa tataggggtg tggaaatagt gatttgagca 3120
cgtcttgaag cgaattcact ggccgtcgtt ttacaacgtc gtgactggga aaaccctggc 3180
gttacccaac ttaatcgcct tgcagcacat ccccctttcg ccagctggcg taatagcgaa 3240
gaggcccgca ccgatcgccc ttcccaacag ttgcgcagcc tgaatggcga atggcgcctg 3300
atgcggtatt ttctccttac gcatctgtgc ggtatttcac accgcatatg gtgcactctc 3360
agtacaatct gctctgatgc cgcatagtta agccagcccc gacacccgcc aacacccgct 3420
gacgcgccct gacgggcttg tctgctcccg gcatccgctt acagacaagc tgtgaccgtc 3480

-continued tccgggagct gcatgtgtca gaggttttca ccgtcatcac cgaaacgcgc gagacgaaag 3540
ggcctcgtga tacgcctatt tttataggtt aatgtcatga taataatggt ttcttagacg 3600
tcaggtggca cttttcgggg aaatgtgcgc ggaaccccta tttgtttatt tttctaaata 3660
cattcaaata tgtatccgct catgagacaa taaccctgat aaatgcttca ataatattga 3720
aaaaggaaga gtatgagtat tcaacatttc cgtgtcgccc ttattccctt ttttgcggca 3780
ttttgccttc ctgtttttgc tcacccagaa acgctggtga aagtaaaaga tgctgaagat 3840
cagttgggtg cacgagtggg ttacatcgaa ctggatctca acagcggtaa gatccttgag 3900
agttttcgcc ccgaagaacg ttttccaatg atgagcactt ttaaagttct gctatgtggc 3960
gcggtattat cccgtattga cgccgggcaa gagcaactcg gtcgccgcat acactattct 4020
cagaatgact tggttgagta ctcaccagtc acagaaaagc atcttacgga tggcatgaca 4080
gtaagagaat tatgcagtgc tgccataacc atgagtgata acactgcggc caacttactt 4140
ctgacaacga tcggaggacc gaaggagcta accgcttttt tgcacaacat gggggatcat 4200
gtaactcgcc ttgatcgttg ggaaccggag ctgaatgaag ccataccaaa cgacgagcgt 4260
gacaccacga tgcctgtagc aatggcaaca acgttgcgca aactattaac tggcgaacta 4320
cttactctag cttcccggca acaattaata gactggatgg aggcggataa agttgcagga 4380
ccacttctgc gctcggccct tccggctggc tggtttattg ctgataaatc tggagccggt 4440
gagcgtgggt ctcgcggtat cattgcagca ctggggccag atggtaagcc ctcccgtatc 4500
gtagttatct acacgacggg gagtcaggca actatggatg aacgaaatag acagatcgct 4560
gagataggtg cctcactgat taagcattgg taactgtcag accaagttta ctcatatata 4620
ctttagattg atttaaaact tcatttttaa tttaaaagga tctaggtgaa gatccttttt 4680
gataatctca tgaccaaaat cccttaacgt gagttttcgt tccactgagc gtcagacccc 4740
gtagaaaaga tcaaaggatc ttcttgagat cctttttttc tgcgcgtaat ctgctgcttg 4800
caaacaaaaa aaccaccgct accagcggtg gtttgtttgc cggatcaaga gctaccaact 4860
ctttttccga aggtaactgg cttcagcaga gcgcagatac caaatactgt ccttctagtg 4920
tagccgtagt taggccacca cttcaagaac tctgtagcac cgcctacata cctcgctctg 4980
ctaatcctgt taccagtggc tgctgccagt ggcgataagt cgtgtcttac cgggttggac 5040
tcaagacgat agttaccgga taaggcgcag cggtcgggct gaacgggggg ttcgtgcaca 5100
cagcccagct tggagcgaac gacctacacc gaactgagat acctacagcg tgagctatga 5160
gaaagcgcca cgcttcccga agggagaaag gcggacaggt atccggtaag cggcagggtc 5220
ggaacaggag agcgcacgag ggagcttcca gggggaaacg cctggtatct ttatagtcct 5280
gtcgggtttc gccacctctg acttgagcgt cgatttttgt gatgctcgtc aggggggcgg 5340
agcctatgga aaaacgccag caacgcggcc tttttacggt tcctggcctt ttgctggcct 5400
tttgctcaca tgttctttcc tgcgttatcc cctgattctg tggataaccg tattaccgcc 5460
tttgagtgag ctgataccgc tcgccgcagc cgaacgaccg agcgcagcga gtcagtgagc 5520
gaggaagcgg aagagcgccc aatacgcaaa ccgcctctcc ccgcgcgttg gccgattcat 5580
taatgcagct ggcacgacag gtttcccgac tggaaagcgg gcagtgagcg caacgcaatt 5640
aatgtgagtt agctcactca ttaggcaccc caggctttac actttatgct tccggctcgt 5700
atgttgtgtg gaattgtgag cggataacaa tttcacacag gaaacagcta tgaccatgat 5760
tacgcca 5767

-continued

<210> SEQ ID NO 4
<211> LENGTH: 14446
<212> TYPE: DNA
<213> ORGANISM: Artificial Sequence
<220> FEATURE:
<221> NAME/KEY: misc_feature
<222> LOCATION: (11862)..(12157)
<223> OTHER INFORMATION: Description of Artificial Sequence: plasmid
vector pTM036. Identity of sequence residues 11862-12157 unknown.

<400> SEQUENCE: 4

```
gaattaattc tcaacacaac atatacaaaa caaacgaatc tcaagcaatc aagcattcta     60

cttctattgc agcaatttaa atcatttctt ttaaagcaaa agcaattttc tgaaaatttt    120

caccatttac gaacgatagc catggctccc ccgcagtgtc tgctgcacac gccttccctg    180

gcttccccac tccttctcct cctcctctgg ctcctgggtg gaggagtggg ggctgagggc    240

cgggaggatg cagagctgct ggtgacggtg cgtgggggcc ggctgcgggg cattcgcctg    300

aagacccccg gggccctgt ctctgctttc ctgggcatcc cctttgcgga gccacccatg    360

ggaccccgtc gctttctgcc accggagccc aagcagcctt ggtcaggggt ggtagacgct    420

acaaccttcc agagtgtctg ctaccaatat gtggacaccc tatacccagg ttttgagggc    480

accgagatgt ggaaccccaa ccgtgagctg agcgaggact gcctgtacct caacgtgtgg    540

acaccatacc cccggcctac atcccccacc cctgtcctcg tctggatcta tgggggtggc    600

ttctacagtg gggcctcctc cttggacgtg tacgatggcc gcttcttggt acaggccgag    660

aggactgtgc tggtgtccat gaactaccgg gtgggagcct ttggcttcct ggccctgccg    720

gggagccgag aggccccggg caatgtgggt ctcctggatc agaggctggc cctgcagtgg    780

gtgcaggaga acgtggcagc cttcgggggt gacccgacat cagtgacgct gtttggggag    840

agcgcgggag ccgcctcggt gggcatgcac ctgctgtccc cgcccagccg gggcctgttc    900

cacagggccg tgctgcagag cggtgccccc aatggaccct gggccacggt gggcatggga    960

gaggcccgtc gcagggccac gcagctggcc caccttgtgg gctgtcctcc aggcggcact   1020

ggtgggaatg acacagagct ggtagcctgc cttcggacac gaccagcgca ggtcctggtg   1080

aaccacgaat ggcacgtgct gcctcaagaa agcgtcttcc ggttctcctt cgtgcctgtg   1140

gtagatggag acttcctcag tgacacccca gaggccctca tcaacgcggg agacttccac   1200

ggcctgcagg tgctggtggg tgtggtgaag gatgagggct cgtattttct ggtttacggg   1260

gccccaggct tcagcaaaga caacgagtct ctcatcagcc gggccgagtt cctggccggg   1320

gtgcgggtcg gggttcccca ggtaagtgac ctggcagccg aggctgtggt cctgcattac   1380

acagactggc tgcatcccga ggacccggca cgcctgaggg aggccctgag cgatgtggtg   1440

ggcgaccaca atgtcgtgtg ccccgtggcc cagctggctg ggcgactggc tgcccagggt   1500

gcccgggtct acgcctacgt ctttgaacac cgtgcttcca cgctctcctg gccccctgtgg   1560

atgggggtgc cccacggcta cgagatcgag ttcatctttg ggatcccccct ggacccctct   1620

cgaaactaca cggcagagga gaaaatcttc gcccagcgac tgatgcgata ctgggccaac   1680

tttgcccgca caggggatcc caatgagccc cgagacccca aggccccaca atggcccccg   1740

tacacggcgg gggctcagca gtacgttagt ctggacctgc ggccgctgga ggtgcggcgg   1800

gggctgcgcg cccaggcctg cgccttctgg aaccgcttcc tccccaaatt gctcagcgct   1860

acctgatagg taccgagctc tctcaacaat ctagctagag tttgctccta tctatatgta   1920

ataaggtatg ctgatatgca ctattcaaat aggagcatta gctatgtttg ttaatgtcac   1980
```

-continued

```
tttatgttat gtgggtaagt cacctaagac actccacgta cctacgttgt tgtctcttac   2040

cggctttaat aaatcttctg cccttgttcc atatttacta attatccctt tcttcactaa   2100

aagaaaattg ttatcattaa gtattagtct ttagaacata tgaggtcttt aattgggtag   2160

gttttacaaa ttaactaata taaaatgtca taaaatccac gtggttaaac aaatgcagaa   2220

aatcgacgtc gtctattgga ccgacagttg ctattaatat aatgggccac catagtagac   2280

tgacaaataa attacctgac aacatcgttt cactaaataa caaacacaaa aagggagtgc   2340

attttccagg gcatttttgt aataaaaaac agttaaaagg gagtgcaata gaaatatagg   2400

ggtgtggaaa tagtgatttg agcacgtctt gaagcgaatt cgagatcggc cgcggctgag   2460

tggctccttc aatcgttgcg gttctgtcag ttccaaacgt aaaacggctt gtcccgcgtc   2520

atcggcgggg gtcataacgt gactccctta attctccgct catgatcaga ttgtcgtttc   2580

ccgccttcag tttaaactat cagtgtttga caggatatat tggcgggtaa acctaagaga   2640

aaagagcgtt tattagaata atcggatatt taaaagggcg tgaaaaggtt tatccgttcg   2700

tccatttgta tgtgcatgcc aaccacaggg ttccccagat ctggcgccgg ccagcgagac   2760

gagcaagatt ggccgccgcc cgaaacgatc cgacagcgcg cccagcacag gtgcgcaggc   2820

aaattgcacc aacgcataca gcgccagcag aatgccatag tgggcggtga cgtcgttcga   2880

gtgaaccaga tcgcgcagga ggcccggcag caccggcata atcaggccga tgccgacagc   2940

gtcgagcgcg acagtgctca gaattacgat caggggtatg ttgggtttca cgtctggcct   3000

ccggaccagc ctccgctggt ccgattgaac gcgcggattc tttatcactg ataagttggt   3060

ggacatatta tgtttatcag tgataaagtg tcaagcatga caaagttgca gccgaataca   3120

gtgatccgtg ccgccctgga cctgttgaac gaggtcggcg tagacggtct gacgacacgc   3180

aaactggcgg aacggttggg ggttcagcag ccggcgcttt actggcactt caggaacaag   3240

cgggcgctgc tcgacgcact ggccgaagcc atgctggcgg agaatcatac gcattcggtg   3300

ccgagagccg acgacgactg gcgctcattt ctgatcggga atgcccgcag cttcaggcag   3360

gcgctgctcg cctaccgcga tggcgcgcgc atccatgccg gcacgcgacc gggcgcaccg   3420

cagatggaaa cggccgacgc gcagcttcgc ttcctctgcg aggcgggttt ttcggccggg   3480

gacgccgtca atgcgctgat gacaatcagc tacttcactg ttggggccgt gcttgaggag   3540

caggccggcg acagcgatgc cggcgagcgc ggcggcaccg ttgaacaggc tccgctctcg   3600

ccgctgttgc gggccgcgat agacgccttc gacgaagccg gtccggacgc agcgttcgag   3660

cagggactcg cggtgattgt cgatggattg gcgaaaagga ggctcgttgt caggaacgtt   3720

gaaggaccga gaaagggtga cgattgatca ggaccgctgc cggagcgcaa cccactcact   3780

acagcagagc catgtagaca acatcccctc ccccttttcca ccgcgtcaga cgcccgtagc   3840

agcccgctac gggctttttc atgccctgcc ctagcgtcca agcctcacgg ccgcgctcgg   3900

cctctctggc ggccttctgg cgctcttccg cttcctcgct cactgactcg ctgcgctcgg   3960

tcgttcggct gcggcgagcg gtatcagctc actcaaaggc ggtaatacgg ttatccacag   4020

aatcagggga taacgcagga aagaacatgt gagcaaaagg ccagcaaaag gccaggaacc   4080

gtaaaaaggc cgcgttgctg gcgtttttcc ataggctccg cccccctgac gagcatcaca   4140

aaaatcgacg ctcaagtcag aggtggcgaa acccgacagg actataaaga taccaggcgt   4200

ttccccctgg aagctccctc gtgcgctctc ctgttccgac cctgccgctt accggatacc   4260

tgtccgcctt tctcccttcg ggaagcgtgg cgcttttccg ctgcataacc ctgcttcggg   4320

gtcattatag cgattttttc ggtatatcca tcctttttcg cacgatatac aggattttgc   4380
```

-continued

```
caaagggttc gtgtagactt tccttggtgt atccaacggc gtcagccggg caggataggt   4440
gaagtaggcc cacccgcgag cgggtgttcc ttcttcactg tcccttattc gcacctggcg   4500
gtgctcaacg ggaatcctgc tctgcgaggc tggccggcta ccgccggcgt aacagatgag   4560
ggcaagcgga tggctgatga aaccaagcca accaggaagg gcagcccacc tatcaaggtg   4620
tactgccttc cagacgaacg aagagcgatt gaggaaaagg cggcggcggc cggcatgagc   4680
ctgtcggcct acctgctggc cgtcggccag ggctacaaaa tcacgggcgt cgtggactat   4740
gagcacgtcc gcgagctggc ccgcatcaat ggcgacctgg gccgcctggg cggcctgctg   4800
aaactctggc tcaccgacga cccgcgcacg gcgcggttcg gtgatgccac gatcctcgcc   4860
ctgctggcga agatcgaaga gaagcaggac gagcttggca aggtcatgat gggcgtggtc   4920
cgcccgaggg cagagccatg actttttttag ccgctaaaac ggccgggggg tgcgcgtgat   4980
tgccaagcac gtccccatgc gctccatcaa gaagagcgac ttcgcggagc tggtgaagta   5040
catcaccgac gagcaaggca agaccgagcg cctttgcgac gctcaccggg ctggttgccc   5100
tcgccgctgg gctggcggcc gtctatggcc ctgcaaacgc gccagaaacg ccgtcgaagc   5160
cgtgtgcgag acaccgcggc cgccggcgtt gtggatacct cgcggaaaac ttggccctca   5220
ctgacagatg aggggcggac gttgacactt gaggggccga ctcacccggc gcggcgttga   5280
cagatgaggg gcaggctcga tttcggccgg cgacgtggag ctggccagcc tcgcaaatcg   5340
gcgaaaacgc ctgattttac gcgagtttcc cacagatgat gtggacaagc ctggggataa   5400
gtgccctgcg gtattgacac ttgaggggcg cgactactga cagatgaggg gcgcgatcct   5460
tgacacttga ggggcagagt gctgacagat gaggggcgca cctattgaca tttgaggggc   5520
tgtccacagg cagaaaatcc agcatttgca agggtttccg cccgtttttc ggccaccgct   5580
aacctgtctt ttaacctgct tttaaaccaa tatttataaa ccttgttttt aaccagggct   5640
gcgccctgtg cgcgtgaccg cgcacgccga aggggggtgc ccccccttct cgaaccctcc   5700
cggcccgcta acgcgggcct cccatccccc caggggctgc gcccctcggc cgcgaacggc   5760
ctcaccccaa aaatggcagc gctggcagtc cttgccattg ccgggatcgg ggcagtaacg   5820
ggatgggcga tcagcccgag cgcgacgccc ggaagcattg acgtgccgca ggtgctggca   5880
tcgacattca gcgaccaggt gccgggcagt gagggcggcg gcctgggtgg cggcctgccc   5940
ttcacttcgg ccgtcggggc attcacggac ttcatggcgg ggccggcaat ttttaccttg   6000
ggcattcttg gcatagtggt cgcgggtgcc gtgctcgtgt tcgggggtgc gataaaccca   6060
gcgaaccatt tgaggtgata ggtaagatta taccgaggta tgaaaacgag aattggacct   6120
ttacagaatt actctatgaa gcgccatatt taaaaagcta ccaagacgaa gaggatgaag   6180
aggatgagga ggcagattgc cttgaatata ttgacaatac tgataagata atatatcttt   6240
tatatagaag atatcgccgt atgtaaggat ttcagggggc aaggcatagg cagcgcgctt   6300
atcaatatat ctatagaatg ggcaaagcat aaaaacttgc atggactaat gcttgaaacc   6360
caggacaata accttatagc ttgtaaattc tatcataatt gggtaatgac tccaacttat   6420
tgatagtgtt ttatgttcag ataatgcccg atgactttgt catgcagctc caccgatttt   6480
gagaacgaca gcgacttccg tcccagccgt gccaggtgct gcctcagatt caggttatgc   6540
cgctcaattc gctgcgtata tcgcttgctg attacgtgca gctttccctt caggcgggat   6600
tcatacagcg gccagccatc cgtcatccat atcaccacgt caaagggtga cagcaggctc   6660
ataagacgcc ccagcgtcgc catagtgcgt tcaccgaata cgtgcgcaac aaccgtcttc   6720
```

-continued

```
cggagactgt catacgcgta aaacagccag cgctggcgcg atttagcccc gacatagccc   6780
cactgttcgt ccatttccgc gcagacgatg acgtcactgc ccggctgtat gcgcgaggtt   6840
accgactgcg gcctgagttt tttaagtgac gtaaaatcgt gttgaggcca acgcccataa   6900
tgcgggctgt tgcccggcat ccaacgccat tcatggccat atcaatgatt ttctggtgcg   6960
taccgggttg agaagcggtg taagtgaact gcagttgcca tgttttacgg cagtgagagc   7020
agagatagcg ctgatgtccg gcggtgcttt tgccgttacg caccaccccg tcagtagctg   7080
aacaggaggg acagctgata gacacagaag ccactggagc acctcaaaaa caccatcata   7140
cactaaatca gtaagttggc agcatcaccc ataattgtgg tttcaaaatc ggctccgtcg   7200
atactatgtt atacgccaac tttgaaaaca actttgaaaa agctgttttc tggtatttaa   7260
ggttttagaa tgcaaggaac agtgaattgg agttcgtctt gttataatta gcttcttggg   7320
gtatctttaa atactgtaga aaagaggaag gaaataataa atggctaaaa tgagaatatc   7380
accggaattg aaaaaactga tcgaaaaata ccgctgcgta aaagatacgg aaggaatgtc   7440
tcctgctaag gtatataagc tggtgggaga aaatgaaaac ctatatttaa aaatgacgga   7500
cagccggtat aaagggacca cctatgatgt ggaacgggaa aaggacatga tgctatggct   7560
ggaaggaaag ctgcctgttc caaaggtcct gcactttgaa cggcatgatg gctggagcaa   7620
tctgctcatg agtgaggccg atggcgtcct ttgctcggaa gagtatgaag atgaacaaag   7680
ccctgaaaag attatcgagc tgtatgcgga gtgcatcagg ctctttcact ccatcgacat   7740
atcggattgt ccctatacga atagcttaga cagccgctta gccgaattgg attacttact   7800
gaataacgat ctggccgatg tggattgcga aaactgggaa gaagacactc catttaaaga   7860
tccgcgcgag ctgtatgatt ttttaaagac ggaaaagccc gaagaggaac ttgtcttttc   7920
ccacggcgac ctgggagaca gcaacatctt tgtgaaagat ggcaaagtaa gtggctttat   7980
tgatcttggg agaagcggca gggcggacaa gtggtatgac attgccttct gcgtccggtc   8040
gatcagggag gatatcgggg aagaacagta tgtcgagcta ttttttgact tactggggat   8100
caagcctgat tgggagaaaa taaaatatta tattttactg gatgaattgt tttagtacct   8160
agatgtggcg caacgatgcc ggcgacaagc aggagcgcac cgacttcttc cgcatcaagt   8220
gttttggctc tcaggccgag gcccacggca agtatttggg caaggggtcg ctggtattcg   8280
tgcagggcaa gattcggaat accaagtacg agaaggacgg ccagacggtc tacgggaccg   8340
acttcattgc cgataaggtg gattatctgg acaccaaggc accaggcggg tcaaatcagg   8400
aataagggca cattgccccg gcgtgagtcg gggcaatccc gcaaggaggg tgaatgaatc   8460
ggacgtttga ccggaaggca tacaggcaag aactgatcga cgcggggttt tccgccgagg   8520
atgccgaaac catcgcaagc cgcaccgtca tgcgtgcgcc ccgcgaaacc ttccagtccg   8580
tcggctcgat ggtccagcaa gctacggcca agatcgagcg cgacagcgtg caactggctc   8640
cccctgccct gcccgcgcca tcggccgccg tggagcgttc gcgtcgtctc gaacaggagg   8700
cggcaggttt ggcgaagtcg atgaccatcg acacgcgagg aactatgacg accaagaagc   8760
gaaaaaccgc cggcgaggac ctggcaaaac aggtcagcga ggccaagcag gccgcgttgc   8820
tgaaacacac gaagcagcag atcaaggaaa tgcagctttc cttgttcgat attgcgccgt   8880
ggccggacac gatgcgagcg atgccaaacg acacggcccg ctctgccctg ttcaccacgc   8940
gcaacaagaa aatcccgcgc gaggcgctgc aaaacaaggt cattttccac gtcaacaagg   9000
acgtgaagat cacctacacc ggcgtcgagc tgcgggccga cgatgacgaa ctggtgtggc   9060
agcaggtgtt ggagtacgcg aagcgcaccc ctatcggcga gccgatcacc ttcacgttct   9120
```

-continued

```
acgagctttg ccaggacctg ggctggtcga tcaatggccg gtattacacg aaggccgagg   9180
aatgcctgtc gcgcctacag gcgacggcga tgggcttcac gtccgaccgc gttgggcacc   9240
tggaatcggt gtcgctgctg caccgcttcc gcgtcctgga ccgtggcaag aaaacgtccc   9300
gttgccaggt cctgatcgac gaggaaatcg tcgtgctgtt tgctggcgac cactacacga   9360
aattcatatg ggagaagtac cgcaagctgt cgccgacggc ccgacggatg ttcgactatt   9420
tcagctcgca ccgggagccg tacccgctca agctggaaac cttccgcctc atgtgcggat   9480
cggattccac ccgcgtgaag aagtggcgcg agcaggtcgg cgaagcctgc gaagagttgc   9540
gaggcagcgg cctggtggaa cacgcctggg tcaatgatga cctggtgcat tgcaaacgct   9600
agggccttgt ggggtcagtt ccggctgggg gttcagcagc cagcgcttta ctggcatttc   9660
aggaacaagc gggcactgct cgacgcactt gcttcgctca gtatcgctcg ggacgcacgg   9720
cgcgctctac gaactgccga taaacagagg attaaaattg acaattgtga ttaaggctca   9780
gattcgacgg cttggagcgg ccgacgtgca ggatttccgc gagatccgat tgtcggccct   9840
gaagaaagct ccagagatgt tcgggtccgt ttacgagcac gaggagaaaa agcccatgga   9900
ggcgttcgct gaacggttgc gagatgccgt ggcattcggc gcctacatcg acggcgagat   9960
cattgggctg tcggtcttca aacaggagga cggccccaag gacgctcaca aggcgcatct  10020
gtccggcgtt ttcgtggagc ccgaacagcg aggccgaggg gtcgccggta tgctgctgcg  10080
ggcgttgccg gcgggtttat tgctcgtgat gatcgtccga cagattccaa cgggaatctg  10140
gtggatgcgc atcttcatcc tcggcgcact taatatttcg ctattctgga gcttgttgtt  10200
tatttcggtc taccgcctgc cgggcggggt cgcggcgacg gtaggcgctg tgcagccgct  10260
gatggtcgtg ttcatctctg ccgctctgct aggtagcccg atacgattga tggcggtcct  10320
gggggctatt tgcggaactg cgggcgtggc gctgttggtg ttgacaccaa acgcagcgct  10380
agatcctgtc ggcgtcgcag cgggcctggc gggggcggtt tccatggcgt tcggaaccgt  10440
gctgacccgc aagtggcaac ctcccgtgcc tctgctcacc tttaccgcct ggcaactggc  10500
ggccggagga cttctgctcg ttccagtagc tttagtgttt gatccgccaa tcccgatgcc  10560
tacaggaacc aatgttctcg gcctggcgtg gctcggcctg atcggagcgg gtttaaccta  10620
cttcctttgg ttccggggga tctcgcgact cgaacctaca gttgtttcct tactgggctt  10680
tctcagcccc agatctgggg tcgatcagcc ggggatgcat caggccgaca gtcggaactt  10740
cgggtccccg acctgtacca ttcggtgagc aatggatagg ggagttgata tcgtcaacgt  10800
tcacttctaa agaaatagcg ccactcagct tcctcagcgg ctttatccag cgatttccta  10860
ttatgtcggc atagttctca agatcgacag cctgtcacgg ttaagcgaga aatgaataag  10920
aaggctgata attcggatct ctgcgaggga gatgatattt gatcacaggc agcaacgctc  10980
tgtcatcgtt acaatcaaca tgctaccctc cgcgagatca tccgtgtttc aaacccggca  11040
gcttagttgc cgttcttccg aatagcatcg gtaacatgag caaagtctgc cgccttacaa  11100
cggctctccc gctgacgccg tcccggactg atgggctgcc tgtatcgagt ggtgattttg  11160
tgccgagctg ccggtcgggg agctgttggc tggctggtgg caggatatat tgtggtgtaa  11220
acaaattgac gcttagacaa cttaataaca cattgcggac gtttttaatg tactggggtg  11280
gtttttcttt tcaccagtga gacgggcaac agctgattgc ccttcaccgc ctggccctga  11340
gagagttgca gcaagcggtc cacgctggtt tgccccagca ggcgaaaatc ctgtttgatg  11400
gtggttccga aatcggcaaa atcccttata aatcaaaaga atagcccgag atagggttga  11460
```

-continued

```
gtgttgttcc agtttggaac aagagtccac tattaaagaa cgtggactcc aacgtcaaag  11520
ggcgaaaaac cgtctatcag ggcgatggcc cactacgtga accatcaccc aaatcaagtt  11580
ttttggggtc gaggtgccgt aaagcactaa atcggaaccc taaagggagc ccccgattta  11640
gagcttgacg gggaaagccg gcgaacgtgg cgagaaagga agggaagaaa gcgaaaggag  11700
cgggcgccat tcaggctgcg caactgttgg gaagggcgat cggtgcgggc ctcttcgcta  11760
ttacgccagc tggcgaaagg gggatgtgct gcaaggcgat taagttgggt aacgccaggg  11820
ttttcccagt cacgacgttg taaaacgacg gccagtgaat tnnnnnnnnn nnnnnnnnnn  11880
nnnnnnnnnn nnnnnnnnnn nnnnnnnnnn nnnnnnnnnn nnnnnnnnnn nnnnnnnnnn  11940
nnnnnnnnnn nnnnnnnnnn nnnnnnnnnn nnnnnnnnnn nnnnnnnnnn nnnnnnnnnn  12000
nnnnnnnnnn nnnnnnnnnn nnnnnnnnnn nnnnnnnnnn nnnnnnnnnn nnnnnnnnnn  12060
nnnnnnnnnn nnnnnnnnnn nnnnnnnnnn nnnnnnnnnn nnnnnnnnnn nnnnnnnnnn  12120
nnnnnnnnnn nnnnnnnnnn nnnnnnnnnn nnnnnnngga tccagatccc gtgggcgaag  12180
aactccagca tgagatcccc gcgctggagg atcatccagc cggcgtcccg gaaaacgatt  12240
ccgaagccca acctttcata gaaggcggcg gtggaatcga aatctcgtga tggcaggttg  12300
ggcgtcgctt ggtcggtcat ttcgaacccc agagtcccgc tcagaagaac tcgtcaagaa  12360
ggcgatagaa ggcgatgcgc tgcgaatcgg gagcggcgat accgtaaagc acgaggaagc  12420
ggtcagccca ttcgccgcca agctcttcag caatatcacg ggtagccaac gctatgtcct  12480
gatagcggtc cgccacaccc agccggccac agtcgatgaa tccagaaaag cggccatttt  12540
ccaccatgat attcggcaag caggcatcgc catgggtcac gacgagatca tcgccgtcgg  12600
gcatgcgcgc cttgagcctg gcgaacagtt cggctggcgc gagcccctga tgctcttcgt  12660
ccagatcatc ctgatcgaca agaccggctt ccatccgagt acgtgctcgc tcgatgcgat  12720
gtttcgcttg gtggtcgaat gggcaggtag ccggatcaag cgtatgcagc cgccgcattg  12780
catcagccat gatggatact ttctcggcag gagcaaggtg agatgacagg agatcctgcc  12840
ccggcacttc gcccaatagc agccagtccc ttcccgcttc agtgacaacg tcgagcacag  12900
ctgcgcaagg aacgcccgtc gtggccagcc acgatagccg cgctgcctcg tcctgcagtt  12960
cattcagggc accggacagg tcggtcttga caaaaagaac cgggcgcccc tgcgctgaca  13020
gccggaacac ggcggcatca gagcagccga ttgtctgttg tgcccagtca tagccgaata  13080
gcctctccac ccaagcggcc ggagaacctg cgtgcaatcc atcttgttca atcatgcgaa  13140
aagatctgga ttgagagtga atatgagact ctaattggat accgagggga atttatggaa  13200
cgtcagtgga gcatttttga caagaaatat ttgctagctg atagtgacct taggcgactt  13260
ttgaacgcgc aataatggtt tctgacgtat gtgcttagct cattaaactc cagaaacccg  13320
cggctgagtg gctccttcaa cgttgcggtt ctgtcagttc caaacgtaaa acggcttgtc  13380
ccgcgtcatc ggcgggggtc ataacgtgac tcccttaatt ctccgctcat gatcttgatc  13440
ccctgcgcca tcagatcctt ggcggcaaga aagccatcca gtttactttg cagggcttcc  13500
caaccttacc agagggcgcc ccagctggca attccggttc gcttgctgtc cataaaaccg  13560
cccagtctag ctatcgccat gtaagcccac tgcaagctac ctgctttctc tttgcgcttg  13620
cgttttccct tgtccagata gcccagtagc tgacattcat ccggggtcag caccgtttct  13680
gcggactggc tttctacgtg ttccgcttcc tttagcagcc cttgcgccct gagtgcttgc  13740
ggcagcgtga agcttgcatg cctgcaggtc aacatggtgg agcacgacac tctcgtctac  13800
tccaagaata tcaaagatac agtctcagaa gaccagaggg ctattgagac ttttcaacaa  13860
```

-continued agggtaatat cgggaaacct cctcggattc cattgcccag ctatctgtca cttcatcgaa 13920
aggacagtag aaaaggaaga tggcttctac aaatgccatc attgcgataa aggaaaggct 13980
atcgttcaag aatgcctcta ccgacagtgg tcccaaagat ggacccccac ccacgaggaa 14040
catcgtggaa aaagaagacg ttccaaccac gtcttcaaag caagtggatt gatgtgataa 14100
cttttcaaca aagggtaata tcgggaaacc tcctcggatt ccattgccca gctatctgtc 14160
acttcatcga aaggacagta gaaaaggaag atggcttcta caaatgccat cattgcgata 14220
aaggaaaggc tatcgttcaa gaatgcctct accgacagtg gtcccaaaga tggaccccca 14280
cccacgagga acatcgtgga aaaagaagac gttccaacca cgtcttcaaa gcaagtggat 14340
tgatgtgata tctccactga cgtaagggat gacgcacaat cccactatcc ttcgcaagac 14400
ccttcctcta tataaggaag ttcatttcat ttggagagga cctcga 14446

<210> SEQ ID NO 5
<211> LENGTH: 1725
<212> TYPE: DNA
<213> ORGANISM: Artificial Sequence
<220> FEATURE:
<223> OTHER INFORMATION: Description of Artificial Sequence: synthetic human acetylcholinesterase gene optimized for expression in plants

<400> SEQUENCE: 5
atgaggcccc cgcagtgtct gctgcacacg ccttccctgg cttccccact ccttctcctc 60
ctcctctggc tcctgggtgg aggagtgggg gctgagggcc gggaggatgc agagctgctg 120
gtgacggtgc gtgggggccg gctgcggggc attcgcctga agacccccgg gggccctgtc 180
tctgctttcc tgggcatccc ctttgcggag ccacccatgg gaccccgtcg ctttctgcca 240
ccggagccca agcagccttg gtcaggggtg gtagacgcta caaccttcca gagtgtctgc 300
taccaatatg tggacaccct atacccaggt tttgagggca ccgagatgtg gaaccccaac 360
cgtgagctga gcgaggactg cctgtacctc aacgtgtgga caccataccc ccggcctaca 420
tcccccaccc ctgtcctcgt ctggatctat gggggtggct tctacagtgg ggcctcctcc 480
ttggacgtgt acgatggccg cttcttggta caggccgaga ggactgtgct ggtgtccatg 540
aactaccggg tgggagcctt tggcttcctg gccctgccgg ggagccgaga ggccccgggc 600
aatgtgggtc tcctggatca gaggctggcc ctgcagtggg tgcaggagaa cgtggcagcc 660
ttcgggggtg acccgacatc agtgacgctg tttggggaga gcgcgggagc cgcctcggtg 720
ggcatgcacc tgctgtcccc gcccagccgg ggcctgttcc acagggccgt gctgcagagc 780
ggtgccccca atggaccctg ggccacggtg ggcatgggag aggcccgtcg cagggccacg 840
cagctggccc accttgtggg ctgtcctcca ggcggcactg gtgggaatga cacagagctg 900
gtagcctgcc ttcggacacg accagcgcag gtcctggtga accacgaatg gcacgtgctg 960
cctcaagaaa gcgtcttccg gttctccttc gtgcctgtgg tagatggaga cttcctcagt 1020
gacaccccag aggccctcat caacgcggga gacttccacg gcctgcaggt gctggtgggt 1080
gtggtgaagg atgagggctc gtattttctg gtttacgggg ccccaggctt cagcaaagac 1140
aacgagtctc tcatcagccg ggccgagttc ctggccgggg tgcgggtcgg ggttccccag 1200
gtaagtgacc tggcagccga ggctgtggtc ctgcattaca cagactggct gcatcccgag 1260
gacccggcac gcctgaggga ggccctgagc gatgtggtgg gcgaccacaa tgtcgtgtgc 1320
cccgtggccc agctggctgg gcgactggct gcccagggtg cccgggtcta cgcctacgtc 1380

-continued

```
tttgaacacc gtgcttccac gctctcctgg cccctgtgga tgggggtgcc ccacggctac   1440

gagatcgagt tcatctttgg gatccccctg gacccctctc gaaactacac ggcagaggag   1500

aaaatcttcg cccagcgact gatgcgatac tgggccaact ttgcccgcac aggggatccc   1560

aatgagcccc gagaccccaa ggccccacaa tggcccccgt acacggcggg ggctcagcag   1620

tacgttagtc tggacctgcg gccgctggag gtgcggcggg ggctgcgcgc ccaggcctgc   1680

gccttctgga accgcttcct ccccaaattg ctcagcgcca cctga                   1725
```

EXPRESSION OF RECOMBINANT HUMAN ACETYLCHOLINESTERASE IN TRANSGENIC PLANTS

REFERENCE TO RELATED APPLICATIONS

This application claims an invention that was disclosed in Provisional Application No. 60/190,440, filed Mar. 17, 2000, entitled "EXPRESSION OF RECOMBINANT HUMAN ACETYLCHOLINESTERASE IN TRANSGENIC TOMATOES." The benefit under 35 U.S.C. § 119(e) of the U.S. Provisional Application is hereby claimed, and the aforementioned application is hereby incorporated herein by reference.

BACKGROUND OF THE INVENTION

1. Field of the Invention

The invention pertains to the field of transgenic plants. More particularly, the invention pertains to the expression of a recombinant form of human acetylcholinesterase in transgenic plants.

2. Description of Related Art

Acetylcholine (ACh) is one of the major signaling molecules in metazoans, functioning mostly as a neurotransmitter in chemical synapses between neurons and in neuromuscular junctions. To ensure a discrete "all-or-none" response across the synapse, the release of ACh is tightly controlled and the neurotransmitter is efficiently removed by the hydrolyzing enzyme, acetylcholinesterase (AChE). In humans, AChE is encoded by a single gene which yields, through alternative splicing of its pre-mRNA, three polypeptide isoforms having distinct C-termini. See Soreq et al., *Proc. Nat. Acad. Sci. U.S.A.* 87: 9688–9692 (1990); Ben Aziz-Aloya et al., *Proc. Natl. Acad. Sci. U.S.A.* 90: 2471–5 (1993); GenBank Accession No. M55040; and U.S. Pat. No. 5,595,903. The complete disclosure of each of the foregoing references is hereby incorporated herein by reference.

Various compounds are well known to inhibit the hydrolyzing activity of AChE. Exposure to such anti-AChE agents leads to over-stimulation of cholinergic pathways, causing muscular tetany, autonomous dysfunction and potentially death. While some naturally occurring AChE inhibitors are very potent, human exposure to them is rare. However, man-made anti-AChE compounds, especially organophosphates (OPs), are widely used as pesticides and pose a substantial occupational and environmental risk. Even more ominous is the fear of deliberate use of OPs as chemical warfare agents against individuals or populations.

Current medical interventions, in the case of acute exposure to anticholinesterase agents, include use of the muscarinic receptor antagonist, atropine, and oximes to reactivate the OP-modified AChE. The reversible carbamate, pyridostigmine bromide, is also used as a prophylactic. However, these conventional treatments have limited effectiveness and have serious short and long-term side effects. In fact, the routine treatments, while successfully decreasing anticholinesterase-induced lethality, rarely alleviate post-exposure delayed toxicity, which may result in significant performance deficits, and even permanent brain damage.

A different approach in treatment and prevention of anti-AChE toxicity seeks to mimic one of the physiological lines of defense against such agents present in mammals. Butyrylcholinesterase (BuChE) is a serum cholinesterase with a broad hydrolytic spectrum that provides protection against a variety of AChE inhibitors. A similar end may be achieved by a variant of AChE found on the membranes of erythrocytes. Both enzymes are believed to serve as circulating scavengers for anti-AChE agents in protection of the vital synaptic AChE. Therefore, administration of cholinesterases could boost their natural potential to counter-act the toxic effects of anti-cholinergic agents. The efficacy of this treatment to protect against a challenge of OPs was tested in a variety of animal models such as mice, rats, guinea pigs, and primates, and was found to be comparable to or better than the currently-used drug regimens in preventing OP-induced mortality without any detrimental side-effects.

Enzyme therapy has the additional benefit of the relatively long half-life time (several days) of the injected enzymes in the blood stream, making it especially useful for prophylaxis. In the foregoing experiments, cholinesterases purified from human or animal blood were used. To be effective, the stoichiometry of cholinesterase to inhibitor must be close to unity. Hence, large amounts of pure, properly folded, stable enzymatic preparations that are free of mammalian pathogens are needed, if enzyme therapy is to be feasible.

Genetically engineered plants have recently been recognized as one of the most cost-effective means for the production of useful recombinant proteins and pharmaceuticals. Therefore, we examined the use of transgenic plants as a cost-effective and safe alternative to the production of human acetylcholinesterase (hAChE) from blood or cell cultures, herein providing the first demonstration of the expression in plants of a key protein component of the nervous system of humans.

SUMMARY OF THE INVENTION

Briefly stated, the invention includes one or more plant cells comprising a polynucleotide that encodes a human acetylcholinesterase.

An embodiment of the invention includes a method of making a transgenic plant that is capable of expressing a physiologically active human acetylcholinesterase, comprising the steps of introducing into at least one plant cell a polynucleotide that encodes a human acetylcholinesterase, and regenerating from the plant cell a transgenic plant that is capable of expressing a physiologically active human acetylcholinesterase in at least one tissue type of the transgenic plant.

Another embodiment of the invention includes a method of making a physiologically active human acetylcholinesterase, comprising the steps of introducing into at least one plant cell a polynucleotide that encodes a human acetylcholinesterase, regenerating from the plant cell a transgenic plant that is capable of expressing a physiologically active human acetylcholinesterase in at least one tissue type of the transgenic plant, and isolating or purifying from the transgenic plant or a part thereof a physiologically active human acetylcholinesterase.

Another embodiment of the invention includes a method of treating a victim of acetylcholinesterase poisoning, comprising the step of administering a therapeutic amount of a physiologically active human acetylcholinesterase expressed in plant tissue.

DETAILED DESCRIPTION OF THE INVENTION

DNA Constructs and Plant Transformation

Figure 1:
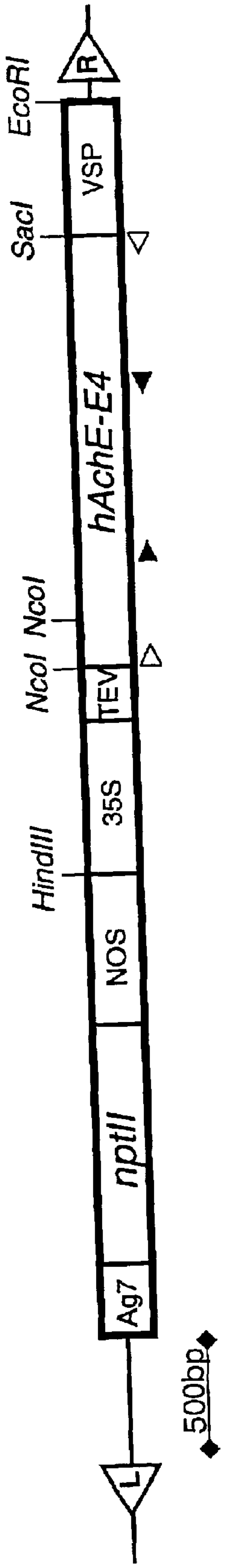
FIG. 1 shows a graphic map of pTM036, the pGPTVkan derivative construct used in the generation of transgenic tomato plants that constitutively express hAChE-E4.

A cDNA encoding human AChE exons II, III and IV was amplified from the plasmid pAChE-E4 (see Sternfeld et al., *J. Neurosci.* 18: 1240–1249 (1990), the complete disclosure of which is hereby incorporated herein by reference) via the polymerase chain reaction (PCR), according to standard methods, which are well known in the art, using the following primers:

```
AChE-Nco - (5'-GATATCTGCAGCCATGgctAGGCCCCCGC) (SEQ ID NO: 1)

AChE-Kpn - (5'-CggtaccTATCAGGTaGCGCTGAGCAATTTG) (SEQ ID NO: 2)
```

The lower case letters in the foregoing primer sequences represent bases that were introduced to create restriction sites for cloning the gene into plant expression vectors. The PCR product was cloned and sequenced using well known methods. An Nco I-Kpn I fragment from a partial digest of pAChE-E4 was cloned into pIBT210.1 (see Haq et al., *Science* 268: 714–716 (1995), the complete disclosure of which is hereby incorporated herein by reference) behind a CaMV 35S promoter and the 5' UTR of Tobacco Etch Virus, and in front of the 3' UTR of the soy bean vspB gene to form pTM034 (FIG. 1, SEQ ID NO:3), according to standard methods, which are well known in the art. A Hind III-Eco RI fragment containing the plant expression cassette was then cloned into the $T_i$ plasmid derivative pGPTV-Kan to form pTM036 (SEQ ID NO:4), using standard methods that are well known in the art. This plasmid was then transferred to *Agrobacterium tumefaciens* strain EHA105, and was used in the subsequent transformation of the *Lycopersicum esculentum* cultivar referred to as "Micro-Tom," as described by Meissner et al. in *Plant J.* 12: 1465–1472 (1997), the complete disclosure of which is hereby incorporated herein by reference.

Genomic PCR, DNA and RNA Blot Analysis

Screening by genomic PCR was performed on 0.8 μg total DNA isolated from kanamycin resistant plants, using the AChE-Nco and AChE-Kpn primers, according to well known methods. For DNA blot analysis, total DNA was prepared, digested with Nco I, and the digested DNA (~20 μg) was resolved by electrophoresis, transferred to a nylon hybridization membrane, and hybridized to a digoxigenin-labeled probe, according to standard methods, which are well known in the art. The digoxigenin-labeled probe was synthesized using the following primers:

```
AChE585for (5'-CGAGAGGACTGTGCTGGTGTC)

AChE1374rev (5'-GTCGCCCACCACATCGCTC)
```

Hybridization and detection were performed according to well known methods. Total RNA was isolated and 5 μg samples were resolved by denaturing formaldehyde gel electrophoresis and transferred to nylon hybridization membranes, according to well known methods.

Acetylcholinesterase Assays and Protein Determination

Plant samples were homogenized in the presence ice-cold extraction buffer (100 mM NaCl, 25 mM Tris, 0.1 mM EDTA, 10 μg/ml leupeptin, pH 7.4, 3 ml per 1 g tissue) using ceramic beads in a bead-beater, and cleared supernatants were collected followed by centrifugation (14,000 rpm). Scaled-down microtiter plate Ellman assays were performed, according to standard methods, which are well known in the art. Cleared extracts (~20 μl) were incubated for 30 minutes at room temperature with 80 μl assay buffer (0.1 M phosphate buffer, pH 7.4) with or without $2\times10^{-5}$ M 1,5-bis(allyldimethylammiumphenyl)pentan-3 one dibromide (BW284c51), which is a specific inhibitor of mammalian AChE. At the end of the 30 minute incubation period, 100 μl of 1 mM 5-5'-dithio-bis(2-nitrobenzoate) (Ellman's reagent) and 2 mM acetylthiocholine in assay buffer was added. Hydrolysis was monitored by measuring optical density at 405 nm at 5 minute intervals for 30 minutes, using a microtiter plate spectrophotometer, plotted against time, and initial rates were calculated from the slope of the linear portion of the graph. Net hydrolysis rates were calculated by subtracting the rates measured in the presence of BW284c15 from those obtained in its absence. To determine the $K_m$, the concentration of the acetylthiocholine substrate in the Ellman's reagent was varied in the range of 0.05–50 mM.

Inhibition curves were obtained by performing the Ellman assay with 1 mM acetylthiocholine in the presence of the indicated concentrations of diethyl p-nitrophenyl phosphate (paraoxon), neostigmine, phehylmethylsulfonyl fluoride (PMSF) or tetraisopropyl pyrophosphoramide (Iso-OMPA). To determine $K_I$ of BW284c51, assays were performed in the presence of 1, 0.33 and 0.25 mM acetylthiocholine, and the inhibitor at $10^{-4}$ to $10^{-10}$ M. Results were then analyzed according to the method of Ordentlich et al. (see Ordentlich et al., *J. Biol. Chem.* 268: 17083–17095 (1993), the complete disclosure of which is hereby incorporated herein by reference). In these experiments, acetylcholinesterase from human erythrocytes was used.

To evaluate the heat stability of the enzyme, plant extracts were incubated for 30 minutes at the indicated temperatures and then assayed as described above. Stability of the enzymatic activity was determined at 4 degrees C. and at 25 degrees C. by incubating plant extracts at the respective temperatures and assaying samples at the indicated time points.

A cDNA encoding exons 2–4 of the human AChE29 gene was inserted into a plant expression cassette driven by the constitutive cauliflower mosaic virus 35S promoter. Referring now to FIG. 1, a graphic map is shown of pTM036, the pGPTVkan derivative construct used in the generation of transgenic tomato plants that constitutively express hAChE-E4. Empty arrowheads denote positions of the PCR primers AChE-Nco and AChE-Kpn used for amplification of the full length coding region of hAChE-E4. Filled arrowheads denote the positions of the PCR primers AChE585 for and AChE1374rev used for the generation of DIG-labeled probe.

We used *Agrobacterium tumefaciens* to construct the tomato explants, and regenerated 27 kanamycin resistant tomato lines. We screened the transformants for the insertion of the recombinant human gene AChE-E4 by PCR. Twelve out of 17 plants tested were positive for the appropriate gene insertion event. The product of the AChE-E4 construct was previously demonstrated to be a monomeric soluble protein, which is fully active in acetylcholine hydrolysis. Therefore, we screened the putative transgenic plants for the expression of specific acetylcholinesterase activity in the soluble protein fraction of leaf extracts of kanamycin-resistant lines.

Figure 2:
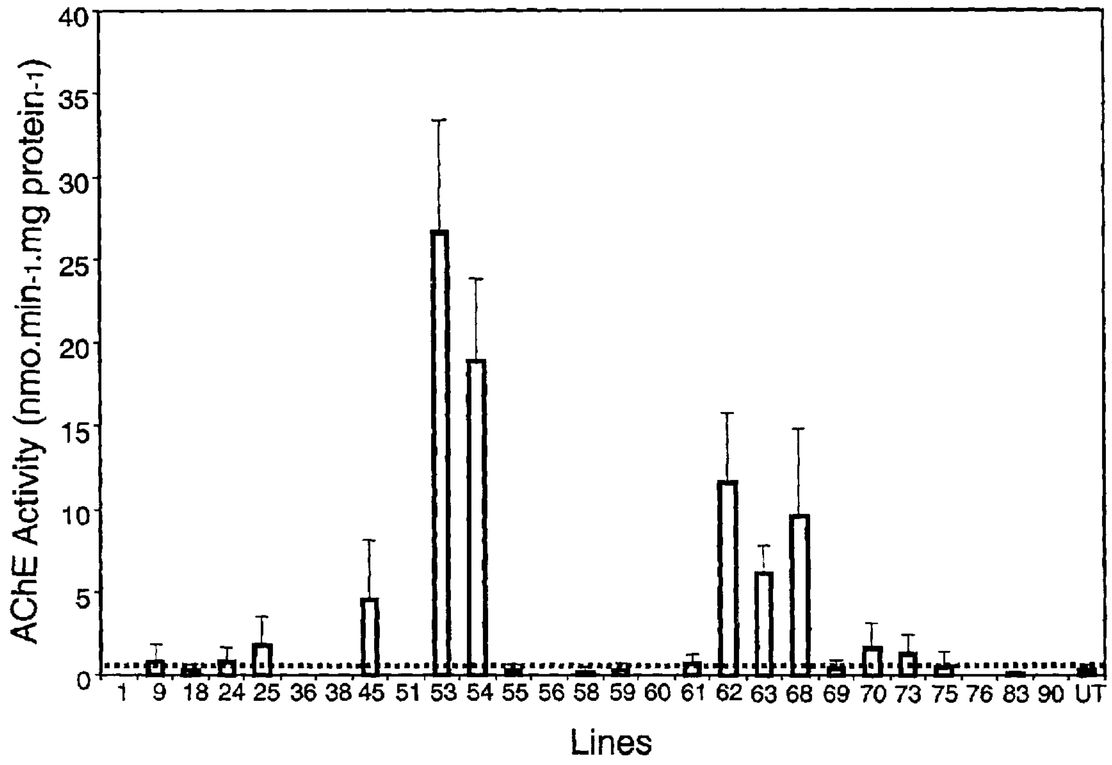
FIG. 2 shows a bar graph depicting high activity of hAChE in transgenic tomato lines.

Referring now to FIG. 2, kanamycin-resistant lines were assayed for specific esterase activity (i.e., total minus activity in the presence of the inhibitor BW284c51) in leaves by the method of Ellman, using acetylthiocholine as a substrate. Protein samples from the indicated transgenic plant lines (AChE-53, 54, 62, 68 and 83), untransformed plant (UT) and a commercially available preparation of AChE from human erythrocytes (E5) were resolved on a non-denaturing gel which was then stained for AChE activity. Plant-derived AChE migrates as a discrete band in non-denaturing gel electrophoresis. On a per soluble protein basis, high activity, comparable to a third of the activity present in mammalian brain and five times more than that present in muscles, was registered in several of the lines, including AChE-53, AChE-54, AChE-62 and AChE-68. In these lines, activity was on the order of 100 mU/g leaf tissue (fresh weight). Acetylcholinesterase present in the transgenic lines appeared as a discrete band in non-denaturing polyacrylamide gels stained for cholinesterase activity. This result demonstrates the apparent uniformity of the protein produced by the plants. No activity was detected in the untransformed line, or in line AChE-83. Unexpectedly, in contrast to the sharp bands of the plant derived recombinant enzyme, the activity of the commercially available preparation of AChE from human erythrocytes appeared as a diffuse smear.

DNA blot analysis revealed that three of the lines that express high levels of activity, AChE-54, AChE-62 and AChE-68, each have one copy of the hAChE-E4 gene inserted in their genomes. Total DNA was isolated from the indicated lines, digested with Nco I, resolved by agarose gel electrophoresis, blotted to nylon membrane and probed with digoxigenin-labeled probe, according to well known methods. Referring to FIG. 2, AChE-83, a transgenic line that does not exhibit AChE activity, has at least two copies of the gene inserted in its genome. However, in this line, the mRNA encoding hAChE-E4 failed to accumulate to detectable levels, as demonstrated by RNA blot analysis, suggesting that transgene silencing in this line might have occurred. RNA blot analysis of several kanamycin-resistant tomato lines indicated that mRNA accumulated to similar levels in all the other lines that were tested. Total RNA was isolated from the indicated lines, resolved by agarose gel electrophoresis, blotted to nylon membrane and stained with methylene blue. The membrane was then probed with AChE specific DIG-labeled probe.

Kinetic Properties of the Plant-Produced Recombinant Enzyme

Figure 3:
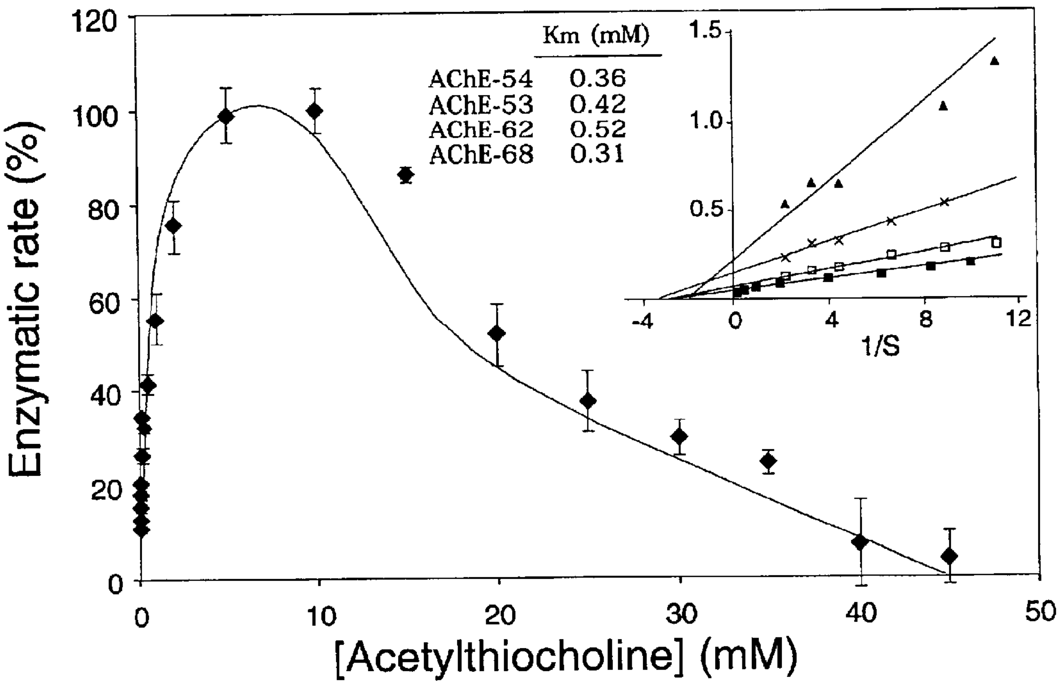
FIG. 3 shows substrate inhibition of recombinant hAChE obtained from transgenic plants.

We calculated the $K_m$ of the plant-derived enzyme for four of our expressing lines to be 0.44±0.10 mM (FIG. 3, inset). This value is similar to that reported for the same molecular form of the enzyme expressed in injected oocytes of *Xenopus laevis* and also to those reported for other forms of the human enzyme. Hydrolysis was inhibited by the presence of substrate at high concentration (FIG. 3), as previously reported for native and recombinant AChE. Enzyme activity was assayed in the presence of acetylthiocholine at 0.05–50 mM, and hydrolysis in the presence of the inhibitor BW284c51 was subtracted at each concentration. A representative high expression line (AChE-54) is shown in FIG. 3. The inset of FIG. 3 shows Lineweaver-Burk analysis for the determination of the $K_m$ for four lines: AChE-53 (squares), AChE-54 (diamonds), AChE-62 (triangles) and AChE-68 (crosses).

Figure 4:
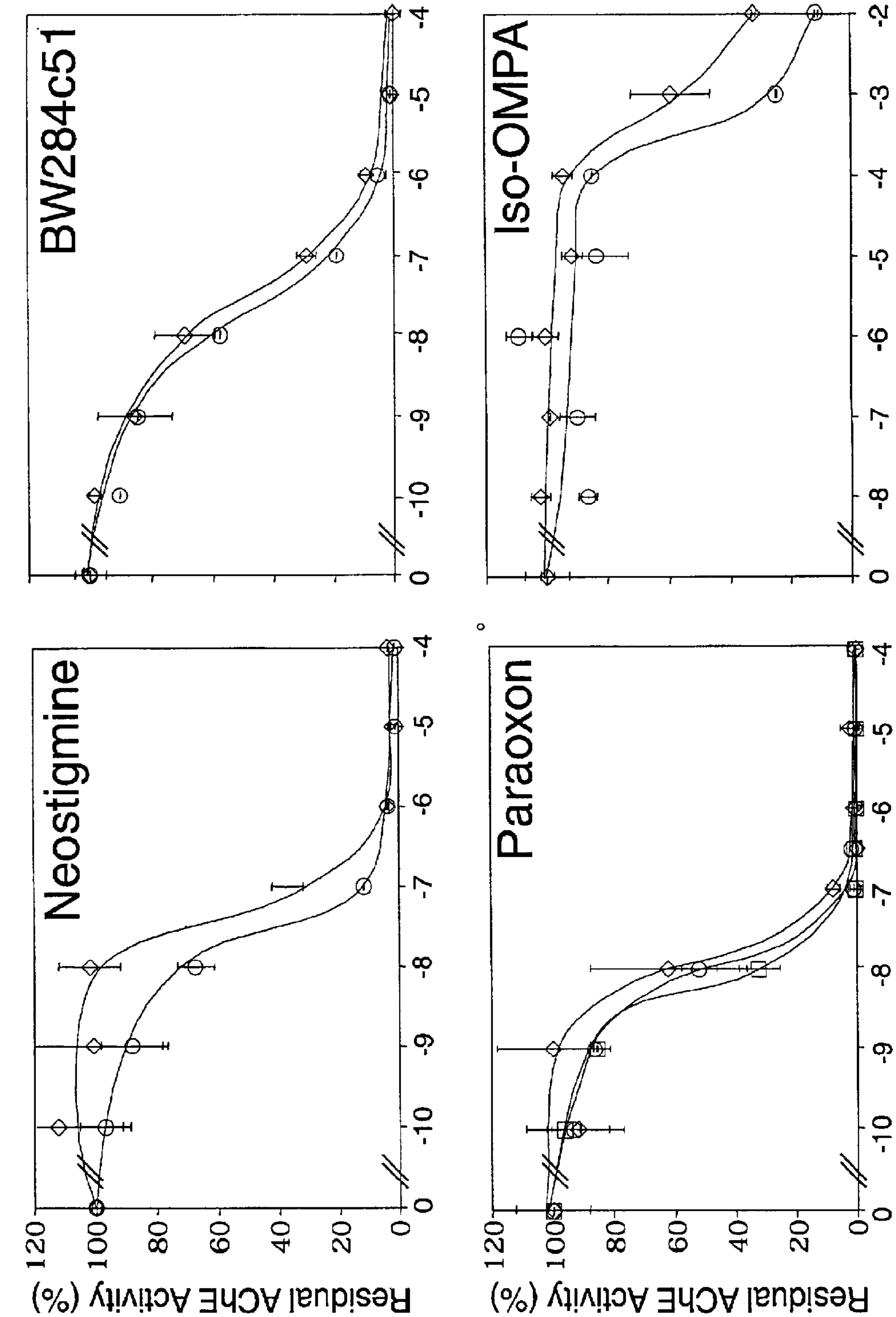
FIG. 4 shows an inhibition profile of AChE obtained from transgenic plants (diamonds), human erythrocytes (circles) and transgenic mice (squares).

AChE inhibitors of various classes, including the reversible inhibitors neostigmine (a carbamate), BW284C51 (an AChE-specific bisquaternary inhibitor), as well as the irreversible inhibitors paraoxon (an organophosphate, the activated form of the pesticide parathion) and PMSF (a general serine hydrolase inhibitor) can inhibit the plant derived recombinant AChE (rAChE), and the inhibition profile is very similar to that of a commercially available preparation of human AChE derived from erythrocytes (FIG. 4). The $K_I$ calculated for BW284c51 is 16 nM, which is in close agreement with the values for the recombinant human synaptic enzyme transiently expressed in mammalian cell cultures (10 nM) and for the erythrocyte form (5 nM). As expected, the butyrylcholinesterase-specific organophosphate, Iso-OMPA, had no effect on either the plant-derived or the erythrocyte-derived enzyme preparations (up to 100 $\mu$M), and only partial inhibition was registered at 10 mM (FIG. 4). The plant-derived E4 enzyme was somewhat less susceptible to paraoxon than an equivalent recombinant enzyme obtained from transgenic mice (FIG. 4).

Figure 5A:
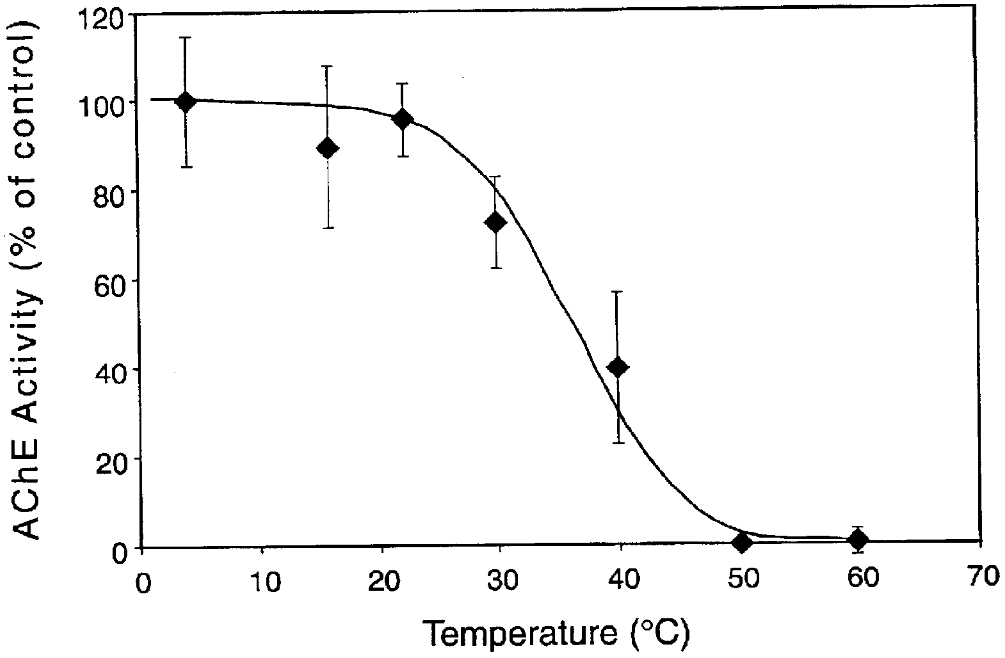
FIG. 5A shows a graph of data indicating that a recombinant hAChE derived from transgenic plants is labile at relatively high temperatures.
Figure 5B:
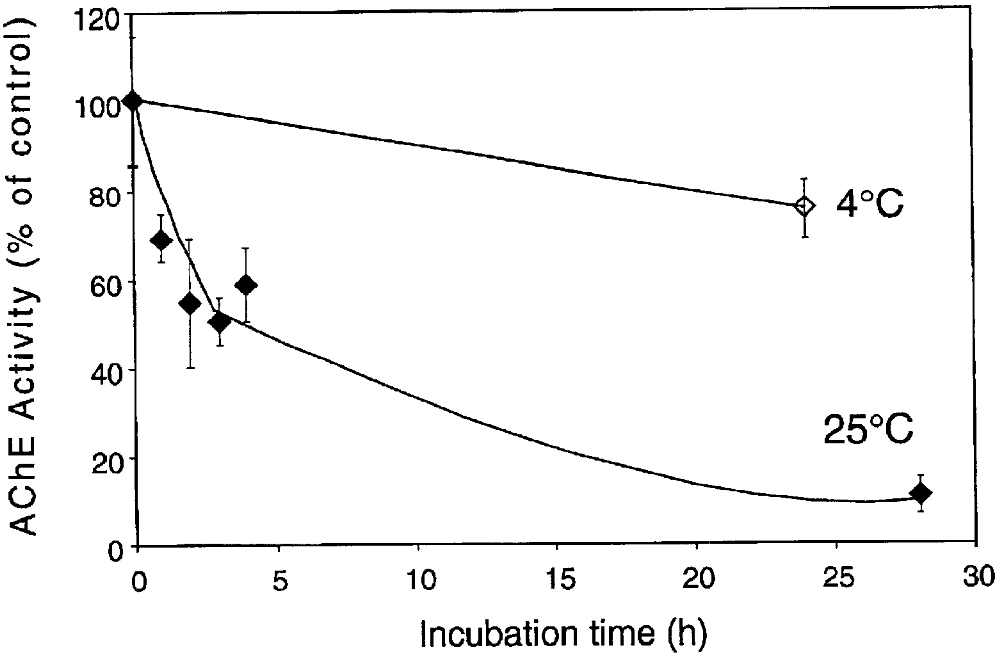
FIG. 5B shows a graph of data indicating that a plant-derived hAChE is relatively stable at room temperature.

The plant-derived hAChE in total soluble protein extracts retained 50% of its initial activity after incubation at 42 degrees for at least 30 minutes (FIG. 5A). Crude leaf extracts were incubated at the indicated temperatures for 30 minutes and then subjected to Ellman's AChE assay. Incubation of plant extracts at room temperature (~25 degrees C.) resulted in gradual loss of AChE activity, with 20% residual activity remaining after 25 hours (FIG. 5B). The activity was very stable at 4 degrees C., with only 20% loss after 24 hours (FIG. 5B). Crude leaf extracts were incubated at 4 degrees C. or at 25 degrees C. for the indicated time periods and then assayed for AChE activity.

Types of Cholinesterases that can be Expressed in Plants

Traditionally, cholinesterases are classified as either acetylcholinesterase (EC 3.1.1.7, AChE) or as butyrylcholine hydrolases (EC 3.1.1.8, BChE, formerly referred to as pseudo-acetylcholinesterase) on the basis of their substrate specificity. While BChE can efficiently hydrolyze substrates with a longer acyl group, the catalytic efficiency of AChE is limited to acetylcholine and, to a lesser degree, propionylcholine. More recently inhibitors have been identified that can selectively inhibit the two types of cholinesterases.

The genes encoding AChE and BChE from several mammals, including humans, have been cloned. Cholinesterases from non-vertebrates and lower vertebrates, even when possessing several different genes, have mixed characteristics. A further complication of the molecular picture is presented by the alternative splicing that the transcript of the AChE gene can undergo leading, in mammals, to three distinct isoforms. These isoforms share a common N-terminal catalytic domain, but diverge in their C-termini, which impact their quaternary structure and membrane association.

The catalytic distinction between the enzymes is not restricted to acyl-choline substrates but to other types of esters. Thus, BChE can catalyze the hydrolysis of cocaine whereas AChE cannot. On the other hand, it was recently demonstrated that the erythrocyte form of AChE can hydrolyze heroin (3,6-diacylmorphine) to morphine, while BChE can hydrolyze heroin only to the intermediate 6-NAM (6-monoacetylmorphine). Interestingly, the synaptic isoform of AChE cannot hydrolyze heroin, making heroin hydrolysis the first reported catalytic distinction between the different isoforms of AChE.

The literature on the non-cholinergic functions of cholinesterases, and especially of AChE, is becoming richer all the time. These proteins apparently play important roles in the developing nervous system and its maintenance, especially in directing the growth of neurons and establishing synaptic connections. The different isoforms have distinct roles through their different C-termini. For example, addition of the synaptic isoform of AChE to cultured neurons has a marked activation effect on neurite outgrowth, and a similar effect has been noted in transgenic frog embryos. In contrast, frog embryos expressing soluble forms of the enzyme do not exhibit such effects.

These small nuances make all of these different isoforms valuable, and we anticipate that plant production of them will be useful for many different ends, including, but not limited to, the following: 1) scavengers of anticholinesterase agents including organophosphates; 2) the hydrolysis of cocaine and heroin in treatment of cases of overdose intoxication by drug abusers; and 3) regeneration of damaged neuronal tissue.

Optimization of the Coding Sequence of hAChE-E4 for Expression in Plants

In most cases, the accumulation of foreign proteins in transgenic proteins is a desirable objective, as it tends to maximize yield and reduce costs of production. Accumulation of proteins is a complex function of many factors that effect synthesis and degradation. By "synthesis" we mean all the biochemical steps which lead to the formation of a mature protein, from transcription of a gene, accumulation of mRNA, translation of messages, localization of products, and many co- and post-translational modifications. Not all of these steps can easily be controlled directly (some, for example, are inherent to the polypeptide in question) and, as yet, not all can be manipulated to enhance accumulation. However, experience has shown that certain optimization measures can have a profound effect on the overall levels of foreign protein accumulation in plants.

Up to the translation stage, the expression of a gene is dependent on the nucleotide sequence not only of the control elements, such as promoter, enhancer elements and 3' sequences, but also on the coding region as well. Molecular cues are encoded by the nucleic acid sequence to allow molecular events, such as termination of transcription, splicing of intervening sequences, rapid turnover of mRNA, and its translatability. Many of these features are common to many different types of organisms, while others are specific for plants, including, for example, intron splice sites, plant-specific RNA stabilizing sequences, and even plant specific biases in codon usage. Thus, optimization of gene sequences entails conforming the coding sequence to those of plant genes.

Numerous methods for the optimization of DNA sequences for increased expression in plants are well known in the art. For example, see U.S. Pat. Nos. 6,180,774; 6,166,302; 6,121,014; 6,110,668; 6,075,185; 6,051,760; 6,043,415; 6,015,891; 6,013,523; 5,994,526; 5,952,547; 5,880,275; 5,877,306; 5,866,421; 5,859,347; 5,859,336; 5,689,052; 5,633,446; 5,625,136; 5,567,862; 5,567,600; 5,545,817; 5,500,365; and 5,380,831, the disclosures of each of which are hereby incorporated herein by reference.

Analysis of the cDNA of hAChE-E4 to Assess its Suitability for Expression in Plants Although we present herein an example wherein the hAChE gene is expressed in tomato plants, the tomato serves here only as a model organism. The expression of hAChE in all major crop plants is intended to be within the scope of the present invention, including (but not restricted to): dicotyledonous plants, such as, for example, tomato, potato, tobacco, legumes (i.e., soybean, peanut, alfalfa), and sweet potato. These plants are typically engineered by Agrobacterium transformation, various suitable methods for which are well known in the art. Monocotyledonous plants are also intended to be within the scope of the present invention, including (but not restricted to): maize, rice, wheat, and barley. These plants are typically engineered by biollistic transformation, various suitable methods for which are well known in the art.

The hAChE-E4 nucleotide sequence includes a total of 574 codons and has an A+T content of 34.8%. Codon use in hAChE-E4 generally is unfavorable for expression in dicots, but acceptable for expression in monocots. In summary, 3.6% of the codons are monocot-unfavorable (including Arg—17.5%, Lys—42.9% and Ser—15.6%), while 12.7% are dicot-unfavorable (including Arg—72.5%, Gly—32.8, Pro—17.6% and Thr—32%), when favorability is defined as making up less than 10% of codon choice for a particular amino acid. Monocot and Dicot preferences were analyzed separately, so as to reveal any potential monocot vs. dicot problems. Tables I and II below summarize total codon use:

TABLE I

| AA | DNA | Dicot Unfavorable | Total | % |
|---|---|---|---|---|
| Ala | GCG | 5 | 53 | 9.5 |
| Arg | CGA | 7 | 40 | 72.5 |
| | CGC | 8 | | |
| | CGG | 14 | | |
| Gly | GGG | 19 | 58 | 32.8 |
| Leu | CTA | 1 | 67 | 1.5 |
| Pro | CGG | 9 | 51 | 17.6 |
| Ser | TCG | 2 | 32 | 6.3 |
| Thr | ACG | 8 | 25 | 32 |
| Other | | | | |
| Total | | 73 | 574 | 12.7 |

TABLE II

| AA | DNA | Monocot Unfavorable | Total | % |
|---|---|---|---|---|
| Arg | CGA | 7 | 40 | 17.5 |
| Ile | ATA | 0 | 9 | 0 |
| Leu | CTA | 1 | 67 | 1.5 |
| | TTA | 0 | | |
| Lys | AAA | 3 | 7 | 42.9 |
| Ser | AGT | 5 | 32 | 15.6 |
| Val | GTA | 5 | 53 | 9.4 |
| STOP | TAA | 0 | 0 | 0 |
| Other | | | | |
| Total | | 21 | 574 | 3.6 |

Based on the data in the foregoing tables, it is evident that some optimization of the native hAChE-E4 nucleotide sequence is desirable, particularly if the gene is to be expressed in dicots. Thus, we present herein an example of a synthetic DNA sequence encoding human acetylcholinesterase that is optimized for expression in plants, referred to herein as SEQ ID NO:5.

Purification of Plant-Produced Cholinesterases

While for some of the potential applications of cholinesterases, no purification would be necessary (e.g., in-vivo bioremediation), and for other applications only partially purified preparations of the enzymes would be necessary (e.g., certain industrial uses, oral administration, topical applications in creams, etc.), for other applications relatively pure enzymes are preferable, and may be required. This is especially true for treating individuals by intra-venous or intra-muscular injections of cholinesterases.

Several published procedures for the purification of acetylcholinesterase are known in the art. See, for example, Fischer et al., *Biotechnol. Appl. Biochem.* 21: 295–311 (1995) and Heim et al., *Biochim. Biophys. Acta* 1396: 306–319 (1998), the complete disclosures of which are hereby incorporated herein by reference. A large scale purification protocol for butyrylcholinesterase based on ammonium sulfate fractionation followed by an batch affinity chromatography should be applicable also for acetylcholinesterase with minor modifications. See, for example, Grunwald et al., *J. Biochem. Biophys. Methods* 34: 123–135 (1997), the complete disclosure of which is hereby incorporated herein by reference.

Additional purification schemes, which are well known in the art, involve engineering a tag to the recombinant enzyme by creating translational fusions. Commercially available plasmids directing such fusions exist mainly for bacterial expression, but can easily be adapted to expression in plants. For example, well known tags that can be used include histidine tags (whereby purification is typically conducted by a nickel-based affinity chromatography); intein-chitin binding tags (whereby purification is conducted by chitin based affinity chromatography and cleavage by a reducing agent, such as dithiothreitol or beta-mercaptoethanol); cellulose binding domains (whereby purification involves affinity chromatography with cellulose). The latter is likely the most useful approach, as it can be done without the addition of any exogenous affinity matrix, since the cholinesterase-CBD fusion binds to cell walls of the plant extract. Release is then mediated by either addition of cellobiose or brief acidification. Cleavage is also possible. For some applications, the cellulose immobilized enzyme-CBD will be extremely useful as a catalytic platform for filters, cellulose based cleaning aids etc.

Further Examples of Applications of the Invention

Administration of exogenous cholinesterases is an efficacious and safe treatment for the prevention of anti-AChE toxicity. In fact, a single pre-treatment injection of either AChE or BuChE may be sufficient for full protection without any post-exposure treatment. However, to ensure maximum protection against a high dosage (equal to several LD50) of OPs, large amounts of the enzymes are required to satisfy the 1:1 stoichiometry required between the enzyme and the inhibitors in the blood. The enzymes can be purified from human or animal blood, or alternatively, they can be expressed in a variety of cell cultures. However, these systems inherently suffer from high costs and risks of contamination with human pathogens. Recombinant cholinesterases of various sources have been expressed in *Escherichia coli*, however, the enzymes thus produced must be denatured and refolded to obtain even partial activity. In addition, they are very labile as compared to the native enzymes. Production by fermentation of yeast cell cultures is also possible, but costs are high and scaling up is expensive.

Therefore, we introduced transgenic plants as a novel production system for human acetylcholinesterase, a key component of cholinergic synapses. Some of the transgenic tomato lines obtained express high levels of AChE activity, with accumulation levels (on a fresh weight basis) as reported for the yeast-derived enzyme (FIGS. 1 and 2). This activity represents authentic human acetylcholinesterase activity, as judged by its enzymatic properties (FIGS. 3 and 4). The plant-derived enzyme is also very stable in the crude plant extract (FIGS. 5A and 5B). Expression levels of the gene product can be increased further by optimizing the coding sequence of the human gene for expression in plants, according to methods that are well known in the art, and by regulating and restricting expression of the gene product to certain tissues.

In humans, AChE is encoded by a single gene which yields, through alternative splicing of its pre-mRNA, three polypeptide isoforms with distinct C-termini. We expressed the engineered AChE-E4 form, encoded by exons 2–4 of the human gene. However, one of ordinary skill in the art will appreciate that the other isoforms can be used as well. AChE-E4 consists of the globular N-terminal domain shared among the three physiological variants of AChE. Expressed by itself, the soluble AChE-E4 polypeptide is a fully competent acetylcholine hydrolase with kinetic properties which are similar to those of the natural forms. This recombinant AChE-E4 variant is especially suited for application as a protective decoy for the neutralization of AChE inhibitors, because its kinetic properties are practically identical to those of synaptic AChE (unlike BuChE). Because it is soluble, it may be cleared more slowly from circulation (unlike the membrane bound AChE forms, which are cleared 50 times faster than soluble BuChE). Because it has the same amino acid sequence as the human enzyme, the plant-derived recombinant hAChE-E4 isoform is expected to be less immunogenic than the heterologous cholinesterases used in previous studies. There are three potential glycosylation sites in human AChE, and glycosylation, which does not affect the enzymatic properties of the enzyme, is important for both the stability of AChE and its pharmacokinetics and its immunogenic properties. As eukaryotes, plants offer the advantage of all forms of post-translational modification, including glycosylation, which, however, differs in details from that in mammals.

Use of the inexpensively produced enzyme is not limited to application by injection, as efficacy of other routes of entry into the body (e.g., orally, inhalation) is expected as well. Lastly, cholinesterases can be incorporated into cleansing preparations, protective skin-creams, filtration devices, and biosensors. For these purposes, the plant-derived enzyme is especially useful, due to lower costs of partial purification and its higher stability.

The extensive use of anticholinesterase pesticides and the concurrent accidental poisoning, the unfortunate threat of OP chemical warfare agents by terrorists and rogue governments, as well as environmental concerns, are the driving force for the development of effective, inexpensive and safe countermeasures and bioremediation solutions. Plant-derived recombinant human AChE is an important step in this direction.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. One or more plant cells comprising a polynucleotide that encodes a human acetylcholinesterase.

2. A tissue culture of regenerable cells derived from the plant cell of claim 1.

3. A transgenic plant, or a part thereof, derived from the plant cell of claim 1.

4. A seed derived from the plant of claim 3.

5. Pollen derived from the plant of claim 3.

6. The plant of claim 3, wherein said plant is capable of expressing a physiologically active human acetylcholinesterase in at least one tissue type of said plant.

7. The plant of claim 3, or a part thereof, wherein said plant is a tomato plant.

8. A method of making a transgenic plant that is capable of expressing a physiologically active human acetylcholinesterase, comprising the steps of:

a) introducing into at least one plant cell a polynucleotide that encodes a human acetylcholinesterase; and b) regenerating from said plant cell a transgenic plant that is capable of expressing said physiologically active human acetylcholinesterase in at least one tissue type of said transgenic plant.

9. A synthetic polynucleotide comprising a nucleic acid molecule that encodes a human acetylcholinesterase.

10. A transformed cell comprising the polynucleotide of claim 9.

11. The plant cell(s) of claim 1, comprising a polynucleotide including a sequence selected from the group consisting of:

a) SEQ ID NO:1;

b) SEQ ID NO:2;

c) SEQ ID NO:3, d) SEQ ID NO:4; and e) SEQ ID NO:5.

* * * * *

UNITED STATES PATENT AND TRADEMARK OFFICE

CERTIFICATE OF CORRECTION

PATENT NO. : 6,770,799 B2 
APPLICATION NO. : 09/810861
DATED : June 15, 2004
INVENTOR(S) : Mor *et al.*

It is certified that error appears in the above-identified patent and that said Letters Patent is hereby corrected as shown below:

Assignee: Boyce Thompson Institute for Plant Research, Inc., Ithaca, NY (USA)

Yissum Research Development Co., Jerusalem (Israel)

Signed and Sealed this

Eighteenth Day of July, 2006

JON W. DUDAS
*Director of the United States Patent and Trademark Office*

UNITED STATES PATENT AND TRADEMARK OFFICE

CERTIFICATE OF CORRECTION

PATENT NO. : 6,770,799 B2
APPLICATION NO. : 09/810861
DATED : August 3, 2004
INVENTOR(S) : Mor et al.

It is certified that error appears in the above-identified patent and that said Letters Patent is hereby corrected as shown below:

Title Page

Insert Item [73] Assignee: Boyce Thompson Institute for Plant Research, Inc., Ithaca, NY (USA)

Yissum Research Development Co., Jerusalem (Israel)

This certificate supersedes certificate of correction issued July 18, 2006.

Signed and Sealed this

Fifth Day of September, 2006

JON W. DUDAS

*Director of the United States Patent and Trademark Office*